United States Patent
Lan et al.

(10) Patent No.: US 9,169,501 B2
(45) Date of Patent: Oct. 27, 2015

(54) METHOD FOR PRODUCING BIODEGRADABLE POLYMER AND BIOMASS FUEL CONVERTED FROM CARBON SOURCE BY RECOMBINANT MICROORGANISMS

(71) Applicant: Yuan Ze University, Chungli, Taoyuan Hsien (TW)

(72) Inventors: Chi-Wei Lan, Taipei (TW); Ho-Shing Wu, Taoyuan (TW); Feng-Shen Chiu, Zhongli (TW)

(73) Assignee: Yuan Ze University, Chungli, Taoyuan Hsien (TW)

( * ) Notice: Subject to any disclaimer, the term of this patent is extended or adjusted under 35 U.S.C. 154(b) by 0 days.

(21) Appl. No.: 14/301,882

(22) Filed: Jun. 11, 2014

(65) Prior Publication Data

US 2014/0295507 A1    Oct. 2, 2014

Related U.S. Application Data

(63) Continuation-in-part of application No. 13/469,945, filed on May 11, 2012, now abandoned.

(51) Int. Cl.

| | |
|---|---|
| *C12P 7/62* | (2006.01) |
| *C12P 7/06* | (2006.01) |
| *C12N 9/04* | (2006.01) |
| *C12N 9/02* | (2006.01) |
| *C12N 9/10* | (2006.01) |
| *C12P 7/08* | (2006.01) |

(52) U.S. Cl.
CPC ............. *C12P 7/625* (2013.01); *C12N 9/0006* (2013.01); *C12N 9/0008* (2013.01); *C12N 9/1029* (2013.01); *C12P 7/06* (2013.01); *C12P 7/08* (2013.01); *C12Y 101/01021* (2013.01); *C12Y 101/01036* (2013.01); *C12Y 102/01003* (2013.01); *C12Y 203/01* (2013.01); *C12Y 203/01009* (2013.01); *Y02E 50/17* (2013.01)

(58) Field of Classification Search
None
See application file for complete search history.

(56) References Cited

U.S. PATENT DOCUMENTS

2005/0239179 A1    10/2005 Skraly et al.

OTHER PUBLICATIONS

Andreessen et al. "Conversion of glycerol to poly(3-hydroxypropionate) in recombinant *Eschrichia coli*" Appl. Environ. Microbiol. (Jan. 2010) 76 (2) 622-626.
Ganesh et al. "Metabolically engineered *Escherichia coli* as a tool for the production of Bioenergy and biochemical from glycerol." Biotech. Bioproc. Engin. (2012) 17, 671-678.

*Primary Examiner* — Nashaat Nashed
(74) *Attorney, Agent, or Firm* — Birch, Stewart, Kolasch & Birch, LLP

(57) ABSTRACT

Disclosed is a method for producing biodegradable polymer and ethanol converted from carbon source by using recombinant microorganisms, comprising the steps of: (A) providing recombinant microorganisms transformed with plasmids containing at least a gene encoding for glycerol utilizing enzyme and a gene encoding for polyhydroxyalkanoate synthase; (B) culturing the recombinant microorganisms in a medium containing glycerol; (C) inducing expression of the genes of step (A), thereby obtaining polyhydroxyalkanoate and ethanol; and (D) recovering the polyhydroxyalkanoate and the ethanol; wherein the recombinant microorganisms have a glycerol utilization rate more than 90% (w/w), and have polyhydroxyalkanoate accumulated therein to a biomass content thereof at least 30% (w/w).

6 Claims, 4 Drawing Sheets

METHOD FOR PRODUCING BIODEGRADABLE POLYMER AND BIOMASS FUEL CONVERTED FROM CARBON SOURCE BY RECOMBINANT MICROORGANISMS

CROSS REFERENCE TO RELATED APPLICATION

This application is a continuation-in-part of U.S. patent application Ser. No. 13/469,945, filed on May 11, 2012, which is incorporated herewith by reference.

BACKGROUND OF THE INVENTION

1. Field of the Invention

The present invention relates generally to a method for producing particular products by recombinant microorganisms, and more particularly, to provide a method for producing biodegradable polymer and biomass fuel converted from carbon source by using recombinant microorganisms.

2. The Prior Arts

With progressing development of bio-diesel, using B2 bio-diesel blend as fuel of vehicles was promoted in Taiwan from 2000. However, the increasing of discarded crude glycerol accompanied with bio-diesel production results in environmental pollution. Although the discarded crude glycerol could be recycled and refined, the economic benefits are limited. Thus, treatment of this crude glycerol, byproduct of production, has becoming the key point for the development of bio-diesel. Regarding the trends of the world, most advanced countries have related laws made for energy policy, and majorities of which have being as principal items for national development. For example, the vehicles using petroleum must be replaced by those using substitute fuels with designate percentage in a given time; as well as increasing the percentage thereof gradually. Under those trends, the production quantities of bio-diesel will be increased relatively, and at that time it will certainly be a serious problem inasmuch as the enormous discarded crude glycerol. Therefore, if the crude glycerol can be efficiently processed and utilized by microorganisms, for example, producing biodegradable polyhydroxyalkanoate (PHA), the additional value resulted from bio-diesel production will be enhanced consequently. PHA, a kind of polyester existing in microorganisms, is generally served as a carbon and energy source. When the microorganisms are in a nutrients-limit condition, they will generate a hydrophobic inclusion body encompassing the PHA within the cell. The hydrophobic granules may have the PHA accumulation content over 90% of their dry weight under certain condition. Concerning the chemical structure, PHA is a kind of polymer composed of hydroxyl fatty acid, i.e., hydroxyalkanoic acid (HA); the structural formula thereof is presented as follows:

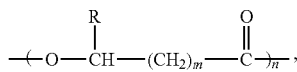

wherein the molecular weight range generally from several ten thousands to several millions, m is 1-4, n is 100-3000, and R is C1-C5. Variable kinds of PHA and monomers thereof differ in R group; in general, PHA compound comprising polyhydroxybutyrate (PHB), polyhydroxyvalerate (PHV), and copolymer of PHB and PHV (i.e., linked both with PHB and PHV), etc. With different kinds of monomer composed,  PHA may not only be a kind of hard and brittle plastics but also a soft elastomer, which involve a series of different characteristics thereof. PHA could be synthesized by using bin-renewable resources isolated from organisms as raw materials; moreover, it could be degraded by organisms, e.g., bacteria, when existing in natural environment, and hence could be a plastic substitute for conventional undegradable plastic. As a biocompatible and biodegradable thermoplastic polymer, it is suggested that PHA will have a good application in medical science and industry.

The production and development of PHA were started in the 1970s. ICI Company produced PHA by using microorganisms in the soil through fermentation process at that time. Meanwhile, Massachusetts Institute of Technology (MIT) introduced engineering techniques to produce PHA by using microorganisms. Owing to the research results, Metabolix Company was derived and established. The patents concerning the abovementioned results were assigned to Zeneca Company, and subsequently assigned to Monsanto Company. Metabolix Company, having purchased related patents from Monsanto Company in 2001, researched and developed on the basis of the techniques from patents and their own, and cooperated afterward with Archer Daniels Midland (ADM) to set up bulk scale production of PHA achieving 50 thousand tons in 2004 and intending to put to production in 2007-2008. The cost for PHA production is US$3-5/kg by fermentation method pertain to Metabolix Company; however, the cost may be reduced to less than US$2-3/kg by industrial process. Therefore, Metabolix Company planned to further abate cost to US$2-3/kg by improving innovative devices. Nevertheless, the highest part of cost is about the medium components employed for fermentation, which accounts for 50-80% of the operation cost. By the analysis of upstream and downstream material cost, the cost of carbon source and nitrogen source is more than 80% of total material cost. As the high cost of carbon source, commercialization and competition of PHA products are obstructed. Thus, if the crude glycerol produced by the bio-diesel factory could be recycled and utilized as a carbon source, it will be beneficial to achieve the objective of cost reduction for PHA production.

On the whole, the national research concerning PHA includes the strain improvement (e.g., *Escherichia coli*, *Wauteria eutropha*), gene mutation (e.g., genes of phaP, phaR), scale-up of culturing volumes, processes for fermentation production, tests for industrial application etc., what is more, the gene research and the strain improvements are both emphasized. In respect of Mainland China, which adopts biodegradable biopolymer material as the main issue for environmental protection of 2008 Beijing Olympic Games; meanwhile, the achievements regarding biodegradable plastics research are also planned to propagandize intensively. Besides, in Korea, the technique of high cell density fermentation for PHA production does have a referring value; moreover, the aspects of bacteria species refinement and the pathway improvement of metabolism also have been studied deeply. Furthermore, the German research group decodes the genomic DNA of *Ralstonia eutropha*, where the homologues genes of phaC, phaB, and phaA are found. It is not only a crucial breakthrough research for *Ralstonia eutropha*, but also could be applied to improve the production of other bacterial species by gene alignment and genetic engineering. In addition, various types of bio-polyester pertained to PHA, e.g., 3-hydroxybutyrate (3HB), 3-hydroxyvalerate (3HV), and 4-hydroxybutyrate (4HB), are produced by using *Bacillus cereus* SPV from the research group of England.

Furthermore, the research group of Switzerland puts emphasis on using genetically modified plants, being different from microbiological expression system, to produce PHA. In U.S.A., other than the studies of bio-polyester production by means of recombinant *E. coli* expression system, the characteristics of copolymer are also analyzed so as to amplify the downstream application fields. Additionally, the research group of Australia deeply research on the gene regulation system of PHA production in bacteria pertained to *Pseudomonas* family, which indicates that the bacteria even of the same family present significant differences in gene level expression. Moreover, the Indian research group uses photosynthesis bacteria for PHA production; and Canada tests the biodegradability of PHA for further research.

SUMMARY OF THE INVENTION

In the light of fast development of bio-diesel, and the demand for PHA production by using microorganisms, it is advantageous to decrease the cost of PHA production if the crude glycerol, produced by biodiesel producing factory, is used as a carbon source for efficient PHA production in recombinant microorganisms.

Accordingly, an objective of the present invention is to provide a method for producing biodegradable polymer and biomass fuel converted from carbon source by using recombinant microorganisms.

In order to improve the shortcoming of conventional skills, the present invention provides a method for producing biodegradable polymer and biomass fuel converted from carbon source by recombinant microorganisms, comprising the steps of: (A) providing recombinant microorganisms transformed with plasmids containing at least a gene encoding for glycerol utilizing enzyme and a gene encoding for polyhydroxyalkanoate synthase; (B) culturing the recombinant microorganisms in a medium containing glycerol; (C) inducing expression of the genes of step (A), thereby obtaining polyhydroxyalkanoate and ethanol; and (D) recovering the polyhydroxyalkanoate and the ethanol; wherein the recombinant microorganisms have a glycerol utilization rate more than 90% (w/w), and have polyhydroxyalkanoate accumulated therein to a biomass content thereof at least 30% (w/w). The recombinant microorganism of the present invention was deposited in the Deutsche Sammlung von Mikroorganismen und Zellkulturen GmbH (DSMZ) located at Inhoffenstr. 7B D-38124 Braunschweig with an accession number DSM 27723 deposited on 12 Sep. 2013.

Preferably, in accordance with the present invention, the gene encoding for glycerol utilizing enzyme may comprise a gene of aldehyde reductase (alrd) and of aldehyde dehydrogenase (aldH), and the gene encoding for polyhydroxyalkanoate synthase may be a gene of PhaCAB polyhydroxyalkanoate synthase. Furthermore, the gene encoding for glycerol utilizing enzyme is constructed in a first expression vector and induced for expression by a first inducer, wherein the preferred first inducer is L-arabinose, and the gene encoding for polyhydroxyalkanoate synthase is constructed in a second expression vector and induced for expression by a second inducer, wherein the preferred second inducer is isopropyl-beta-D-thiogalactopyranoside (IPTG). The recombinant microorganisms are incubated at a temperature of 25° C. to 37° C. under anaerobic or aerobic conditions, and the inoculation rate is more than 3% (v/v). The recombinant microorganisms may be Prokaryotes, preferably *Escherichia coli*, or Eukaryotes.

According to an embodiment of the present invention, the recombinant microorganisms transformed with dual plasmids are induced for expression by two stage gene regulation, wherein the aldehyde reductase and aldehyde dehygrogenase are induced with L-arabinose and the polyhydroxyalkanoate synthase with IPTG respectively both under aerobic conditions. Consequently, the recombinant microorganisms have a glycerol utilization rate more than 90% (w/w), which is 2-folded than that of non-transformed wild-type, and have polyhydroxyalkanoate accumulated therein to a biomass content thereof at least 30% (w/w) as a result of conversion of glycerol. The present invention provides a method to solve the problem of environmental pollution accompanied with the development of energy substitute and creates added-value thereof by means of employing microorganisms for conversion of glycerol to polyhydroxyalkanoate and bioethanol. Furthermore, the present invention is here to improve the defect of higher cost for fermentation process (e.g., the cost of nitrogen source, antibiotics and inducers) while the quantity of production does not reach the scale of bulk production. In accordance with the present invention, the discarded crude glycerol brought by biodiesel factory can be directly used as nutrition source for the recombinant culture while proceeding metabolism and synthesis. Therefore, the issues rose by the excess of crude glycerol, and environmental pollution can be readily resolved. The environmental friendly plastics of polyhydroxyalkanoate and bioethanol produced by the present invention could also be applied in many fields, such as biotechnology industry, food manufactures, chemical materials and products manufactures, medical industry, etc. in the future.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying tables and drawings are included to provide a further understanding of the invention, and are incorporated in and constitute a part of this specification. The tables and drawings illustrate embodiments of the invention and, together with the description, serve to explain the principles of the invention.

The present invention generally provides a method for producing biodegradable polymer and biomass fuel converted from carbon source by using recombinant microorganisms, wherein at least a gene encoding for glycerol utilizing enzyme and a gene encoding for polyhydroxyalkanoate synthase are co-transformed into microorganisms, and then incubates the recombinant microorganisms in a medium containing glycerol (for example, crude glycerol with the purity over 70%). By two stage gene regulation for gene expression, L-arabinose as an inducer is added to induce the expression of aldehyde reductase (alrd) and aldehyde dehygrogenase (aldH). In addition, IPTG as well as an inducer is added respectively to induce the expression of polyhydroxyalkanoate synthase. By way of the metabolic synthesis in the recombinant microorganisms, polyhydroxyalkanoate, a biodegradable polymer, and bioethanol are produced therefrom. The non-transformed wild-type microorganisms has only 50% crude glycerol utilization rate and cannot produce polyhydroxyalkanoate due to the deficiency of polyhydroxyalkanoate synthase. However, the recombinant microorganisms provided by the present invention, cultured under aerobic conditions, have more than 90% crude glycerol utilization rate, which is 2-folded than that of wild-type microorganisms, and can produce polyhydroxyalkanoate with an accumulation content above 30% (w/w).

Figure 1:
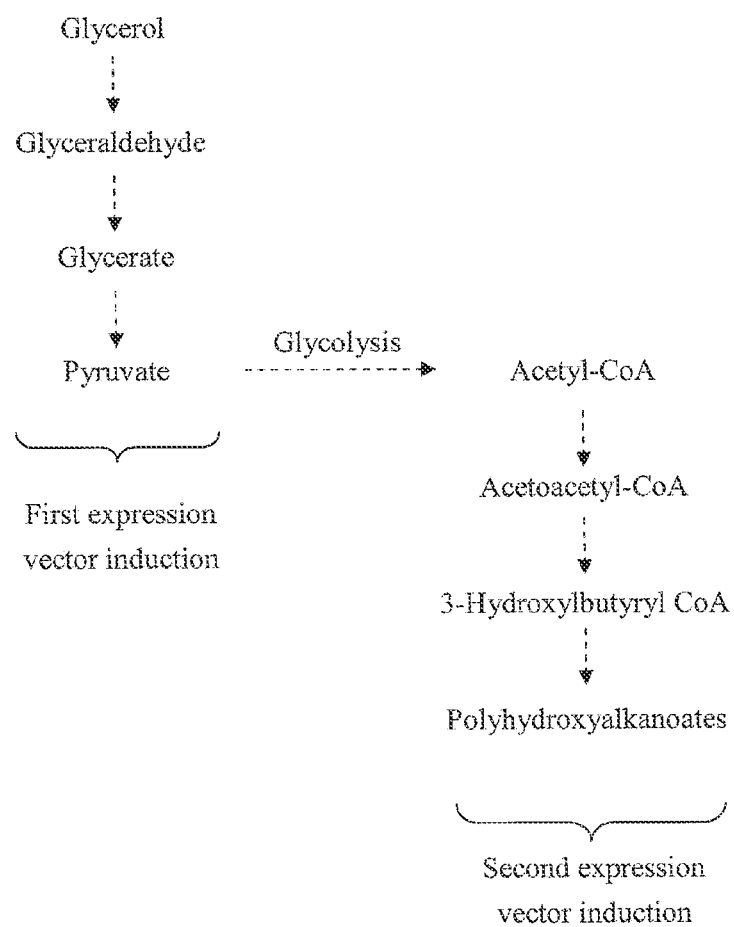
FIG. 1 shows the strategy for dual plasmids construction according to an embodiment of the present invention.

Some bacteria could produce polyhydroxyalkanoate and accumulate therein dependent on the various biosynthesis pathway and the kind of enzymes applied as well as the specificity for their substrate. Due to different pathways and enzyme specificity, polyhydroxyalkanoate presents various polymorphism of monomer structure, including 3-hydroxy fatty acid (e.g., 3-hydroxypropionic acid, extending to 3-hydroxypalmitic acid and a series of members thereof) and 4-, 5-, 6-hydroxy fatty acid; furthermore, 3-hydroxy fatty acid with unsaturated side group, methyl group, and other functional groups are also served as the monomer unit thereof. The present invention performing the pathway of PHA synthesis from Acetyl-CoA, and the strategy for dual plasmids expression in recombinant microorganisms are shown as FIG. 1. Firstly, the glycerol, as a carbon source, is converted to pyruvate by the enzymes expressed from the first expression vector. The pyruvate is then converted to acetyl-CoA via glycolsis, and acetoacetyl-CoA is synthesized by condensing two acetyl-CoA molecules via β-ketothiolase (PhaA). Acetoacetyl-CoA is then catalyzed by NADPH-dependent acetoacetyl-CoA reductase (PhaB) to 3-hydroxylbutyrl CoA, which is polymerized by PHA synthase (PhaC) and led to the synthesis of polyhydroxyalkanoate finally.

EXAMPLE 1

Establishment of Recombinant E. coli (Dual-Plasmid)

Figure 2:
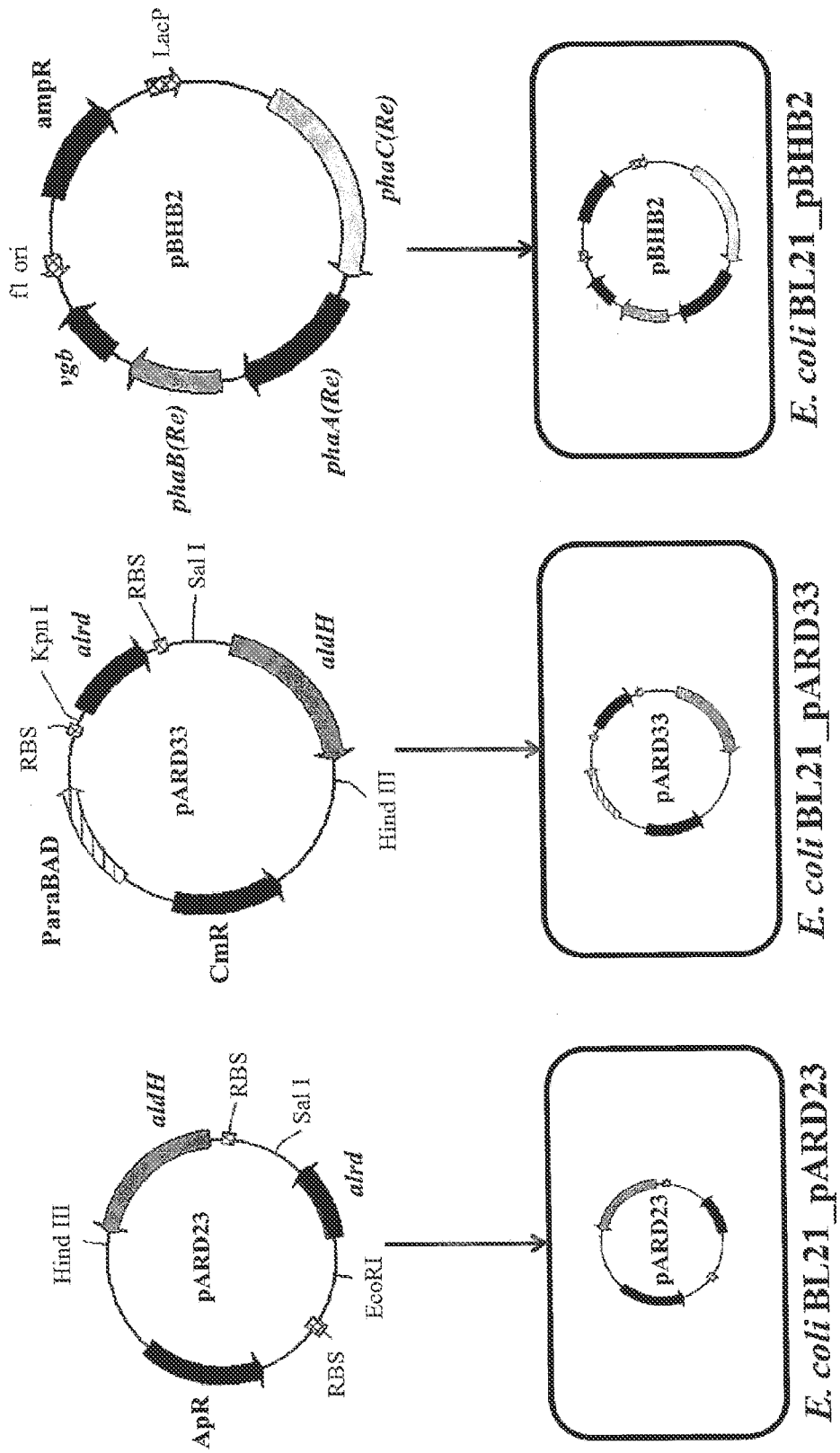
FIG. 2 is a schematic view showing the expression vectors of pARD23, pARD33 and pBHB2 according to an embodiment of the present invention.
Figure 3:
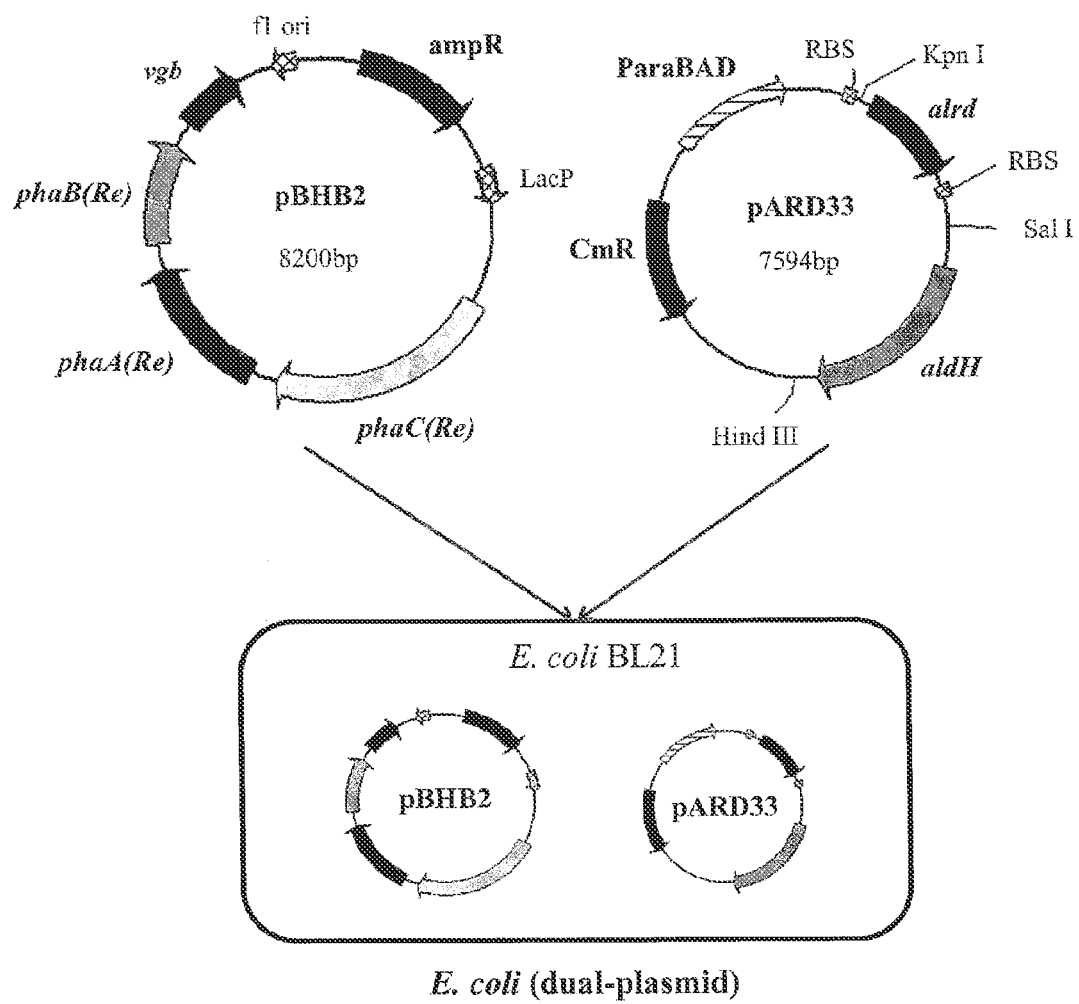
FIG. 3 is a schematic view showing the recombinant microorganisms having two plasmids co-transformed with pARD33 and pBHB2 according to an embodiment of the present invention.

The *E. coli* strains and plasmids used by the present invention are listed as Table 1. The genomic DNA of *R. eutropha* H16 is extracted at first. The gene of aldehyde reductase (alrd) and aldehyde dehygrogenase (aldH) are amplified by polymerase chain reaction (PCR) using abovementioned genomic DNA as temples. The DNA fragments amplified are confirmed by electrophoresis and then cloned to the expression vectors of high-copy pET-23a vector and low-copy pBAD33 vector respectively. In addition, the genes of phaC, phaB and phaA (hereinafter to be referred as phaCAB) encoding for polyhydroxyalkanoate synthase are also isolated from *R. eutropha* H16 and cloned to pBluescript II KS expression vector. The resulting pARD23, pARD33 and pBHB2 plasmids are then transformed to *E. coli* BL21, respectively (shown in FIG. 2). Afterwards, abovementioned BL21 clones each with single plasmid are induced for expression, and the level of expressed mRNA, the activities of proteins, and the crude glycerol utilization rate are detected and analyzed. The clones with pARD33 plasmid which show higher crude glycerol utilization rate are selected. Subsequently, a recombinant *E. coli* (dual-plasmid) clone co-transformed with pARD33 and pBHB2 plasmid is established (shown in FIG. 3), which is then analyzed by detection of crude glycerol utilization rate and PHB accumulation. The recombinant *E. coli* (dual-plasmid) clone was deposited in the Deutsche Sammlung von Mikroorganismen und Zellkulturen GmbH (DSMZ) on 12 Sep. 2013, with an accession number DSM 27723.

TABLE 1

| | Description |
|---|---|
| Strains | |
| R. eutropha H16 | Wild-type |
| E. coli DH5α | Wild-type |
| E. coli BL21 | Wild-type |
| E. coli XL1-BLUE | pBHB2 |
| Plasmids | |
| pGEM-T easy | Cloning vector |
| pET-23a | High level expression vector |
| pBAD33 | Expression vector |
| pGEM-T easy_alrd | pGEM-T easy :: alrd$_{Re}$ |
| pGEM-T easy_aldH | pGEM-T easy :: aldH$_{Re}$ |
| pBHB2 | pBluescript II KS :: phaCAB$_{Re}$ |
| pARD23 | pET-23a :: alrd/aldH |
| pARD33 | pBAD33 :: alrd/aldH |

EXAMPLE 2

Fermentation by Shaking Incubation

Define medium is used for incubation according to the present embodiment, by which the effects of additional carbon and nitrogen source, growing conditions, and the induction concentration are intended to be determined.

(1) Comparison of *E. coli* (WT) and *E. coli* (Dual-Plasmid)

Multiple 500 ml flasks are prepared, in which 3 ml of test clones are inoculated (more than 3%) in medium with total volumes of 100 ml having 30 g/L glycerol and 2 g/L yeast extracts. The prepared medium are then incubated at 37° C. (25-37° C. are available) with shaking at 200 rpm. In order to analyze the growth conditions, medium are monitored by optical density detection at 600 nm with spectrophotometer. Further, crude glycerol utilization rate and PHA accumulation content are analyzed by means of high performance liquid chromatography (HPLC) and gas chromatography (GC).

The results according to the present embodiment are shown in Table 2. As seen from the table, the dry cell weight (DCW), crude glycerol utilization rate, PHA accumulation content, $Y_{p/s}$ and $d_{s/t}$ of *E. coli* (dual-plasmid) are all significantly better than that of the wild type *E. coli* (namely *E. coli* (WT)). It indicates that the Alrd and AldH, as glycerol utilizing enzymes, and PhaCAB, as a polyhydroxyalkanoate synthase, are both expressed and functional.

TABLE 2

Fermentation products of *E. coli* (WT) and *E. coli* (dual-plasmid)

| | DCW (g L$^{-1}$) | PHB cont. (w/w) | PHB conc. (g L$^{-1}$) | CG reduce conc. (g L$^{-1}$) cont. (w/w) | $Y_{x/s}$ (g g$^{-1}$) | $Y_{p/s}$ (g g$^{-1}$) | $Y_{p/t}$ (g h$^{-1}$) | $d_{s/t}$ (g h$^{-1}$) |
|---|---|---|---|---|---|---|---|---|
| *E. coli* (WT) | 3.68 | — | — | 15.98; 51.5 | 0.23 | — | — | 0.33 |
| *E. coli* (dual-plasmid) | 6.47 | 30.2 | 1.95 | 28.76; 98.2 | 0.23 | 0.07 | 0.04 | 0.60 |

CG reduce concentration: consumed crude glycerol concentration
$Y_{x/s}$: Yield of biomass from substrate; substrate here is crude glycerol
$Y_{p/s}$: Yield of product from substrate; substrate here is crude glycerol
$Y_{p/t}$: productivity of product
$d_{s/t}$: Digestion rate of substrate; substrate here is crude glycerol (2) Comparison of *E. coli* (WT) and *E. coli* (Dual-Plasmid) Under Induction The objective of the present embodiment is to analyze the PHA expression under induction by using inducers of L-arabinose and IPTG. The experimental procedures performed is as the same as abovementioned, but the inducers are added. The results are shown in Table 3. Referring to Table 3, the glycerol utilization rate of *E. coli* (dual-plasmid) is higher than that of *E. coli* (WT) whether with inducer or not. The PHA accumulation content of *E. coli* (dual-plasmid) is more than 29%. While under conditions with inducer, the glycerol utilization rate and the PHA accumulation content of *E. coli* (dual-plasmid) are both superior than that of under no inducer condition. Accordingly, the present invention will perform an incubation condition with inducers.

TABLE 3

Fermentation products of *E. coli* (WT) and *E. coli* (dual-plasmid) under induction

| | Ind. | DCW (g L$^{-1}$) | PHB cont. (w/w) | PHB conc. (g L$^{-1}$) | CG reduce conc. (g L$^{-1}$) cont. (w/w) | $Y_{x/s}$ (g g$^{-1}$) | $Y_{p/s}$ (g g$^{-1}$) | $Y_{p/t}$ (g h$^{-1}$) | $d_{s/t}$ (g h$^{-1}$) |
|---|---|---|---|---|---|---|---|---|---|
| *E. coli* (WT) | x | 3.68 | — | — | 15.98; 51.5 | 0.23 | — | — | 0.33 |
| *E. coli* (dual-plasmid) | x | 5.72 | 21.39 | 1.22 | 29.90; 85.21 | 0.19 | 0.04 | 0.03 | 0.62 |
| | v | 6.23 | 29.23 | 1.82 | 32.61; 95.49 | 0.19 | 0.06 | 0.04 | 0.68 |

CG reduce concentration: consumed crude glycerol concentration
$Y_{x/s}$: Yield of biomass from substrate; substrate here is crude glycerol
$Y_{p/s}$: Yield of product from substrate; substrate here is crude glycerol
$Y_{p/t}$: productivity of product
$d_{s/t}$: Digestion rate of substrate; substrate here is crude glycerol (3) Test of *E. coli* (Dual-Plasmid) Under Anaerobic Conditions To increase the cell density suitable for testing, previously described tests with various conditions such as incubation time, incubation temperature and being with inducer or not, are all employed under aerobic conditions. On the basis of the previous preferable conditions, the recombinant microorganisms are further tested under anaerobic conditions with the same growth conditions, analytic procedures and methods. *E. coli* (WT) and *E. coli* (dual-plasmid) are both incubated at 37° C. for 9 hours with inducer IPTG so as to synthesize PHA; the results are shown in Table 4. Although the anaerobic environment is unfavorable for growth of *E. coli* (WT) and *E. coli* (dual-plasmid), *E. coli* (dual-plasmid) can still synthesize PHA thereunder. Comparing to the results incubated under aerobic conditions, *E. coli* (dual-plasmid) has a more outstanding expression result whether under anaerobic or aerobic conditions than that of *E. coli* (WT); whereas, it is necessary to sustain under aerobic conditions when aiming to reach high cell density incubation.

TABLE 4

Products of *E. coli* (dual-plasmid) incubated under anaerobic conditions

| | Ind. | DCW (g L$^{-1}$) | PHB cont. (w/w) | PHB conc. (g L$^{-1}$) | $Y_{p/t}$ (g h$^{-1}$) |
|---|---|---|---|---|---|
| *E. coli* (WT) | x | 0.06 | — | — | — |
| *E. coli* (dual-plasmid) | v | 0.56 | 27.70 | 0.15 | 0.003 |

CG reduce concentration: consumed crude glycerol concentration
$Y_{x/s}$: Yield of biomass from substrate; substrate here is crude glycerol
$Y_{p/s}$: Yield of product from substrate; substrate here is crude glycerol
$Y_{p/t}$: productivity of product
$d_{s/t}$: Digestion rate of substrate; substrate here is crude glycerol

EXAMPLE 3

Fermentation in Bioreactor

In accordance with Example 2, the culturing condition for high cell density incubation was determined, wherein the crude glycerol served as an only carbon source is added in a define medium, and L-arabinose and IPTG are then added respectively to induce the expression of glycerol utilizing enzymes and PHA synthase by enforcing *E. coli* (dual-plasmid) to proceed glycerol metabolism so as to produce PHA. In order to evaluate the condition suitable for bulk production of PHA, fermentation in bioreactor is performed according to the present embodiment. The results of fermentation are shown in Table 5. As results shown, although the content of PHA accumulation is fewer than 30% (w/w), however, the glycerol utilizing rate reaches to 94% (w/w). Therefore, the objective of the present invention is achieved.

TABLE 5

Products of *E. coli* (dual-plasmid) incubated in bioreactor

| | Ind. | DCW (g L$^{-1}$) | PHB cont. (w/w) | PHB conc. (g L$^{-1}$) | CG reduce conc. (g L$^{-1}$); cont. (w/w) | $Y_{x/s}$ (g g$^{-1}$) | $Y_{p/s}$ (g g$^{-1}$) | $Y_{p/t}$ (g h$^{-1}$) | $d_{s/t}$ (g h$^{-1}$) |
|---|---|---|---|---|---|---|---|---|---|
| *E. coli* (dual-plasmid) | v | 6.65 | 20.05 | 1.33 | 39.25; 94.05 | 0.17 | 0.03 | 0.03 | 0.82 |

CG reduce concentration: consumed crude glycerol concentration
$Y_{x/s}$: Yield of biomass from substrate; substrate here is crude glycerol
$Y_{p/s}$: Yield of product from substrate; substrate here is crude glycerol
$Y_{p/t}$: productivity of product
$d_{s/t}$: Digestion rate of substrate; substrate here is crude glycerol

EXAMPLE 4

Production of Ethanol

Figure 4:
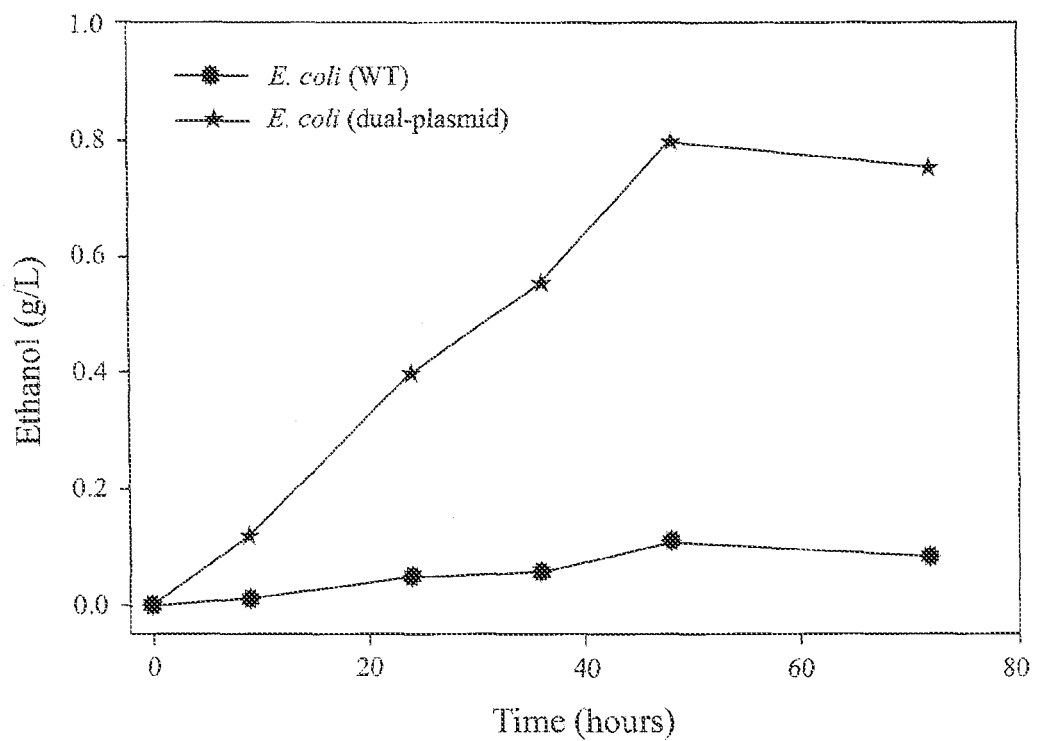
FIG. 4 is a graph showing the results of ethanol yield of *E. coli*, (dual-plasmid) from shaking incubation according to an embodiment of the present invention.

The culturing conditions established by shaking fermentation in example 2 for high cell density incubation is employed by the present embodiment to demonstrate the feasibility for ethanol production. The recombinant *E. coli* (dual-plasmid) according to the present invention is incubated in a define medium containing crude glycerol as an only carbon source, and added with L-arabinose and IPTG as inducers for inducing the expression of glycerol utilizing enzymes and PHA synthase at 37° C. with shaking at 200 rpm for 72 hours; the results are shown in FIG. 4. As indicated in FIG. 4, it is confirmed that the recombinant *E. coli* (dual-plasmid) according to the present invention, by the strategy of dual plasmids expression, not only uptaking glycerol in large quantities but also producing ethanol of a yield of 0.8 g/L, which is much higher, namely 8-folded, than 0.1 g/L of *E. coli* (WT).

The present invention utilizes recombinant microorganisms as a vehicle to produce polyhydroxyalkanoate by glycerol metabolism, in which the carbon source including glucose and glycerol etc. can be readily converted to polyhydroxyalkanoate and ethanol without needs of PH regulation. Although the present invention takes Prokaryotes, e.g. *E. coli*, as expression host cell for example, it is also available to use Eukaryotes such as *Pichia pastoris*, a kind of yeast, as expression host cell.

As embodiments mentioned above, the present invention providing a method for producing biodegradable polymer and biomass fuel using recombinant microorganisms is subject to the utility demand. Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method for producing biodegradable polymer and ethanol converted from carbon source, comprising the steps of:
  (A) providing *E. coli* DSM 27723, said *E. coli* DSM 27723 containing plasmids encoding aldehyde reductase (alrd), aldehyde dehydroxygenase (aldH), and PhaCAB polyhydroxyalkanoate synthase;
  (B) culturing the *E. coli* DSM 27723 in a medium containing glycerol;
  (C) inducing expression of the *E. coli* DSM 27723 plasmid encoded aldehyde reductase (alrd), aldehyde dehydroxygenase (aldH), and PhaCAB polyhydroxyalkanoate synthase, thereby obtaining polyhydroxyalkanoate and ethanol; and
  (D) recovering the polyhydroxyalkanoate and the ethanol;
  wherein the recombinant microorganisms utilize more than 90% of the glycerol as a substrate (w/w), and have polyhydroxyalkanoate accumulated therein to a biomass content thereof of at least 30% (w/w).

2. The method according to claim 1, wherein the plasmid encoded aldehyde reductase (alrd) and aldehyde dehydroxygenase (aldH) are induced separately from the plasmid encoded PhaCAB polyhydroxyalkanoate synthase.

3. The method according to claim 2, wherein the plasmid encoded aldehyde reductase (alrd) and aldehyde dehydroxygenase (aldH) are induced by L-arabinose.

4. The method according to claim 2, wherein the plasmid encoded PhaCAB polyhydroxyalkanoate is induced by isopropyl-beta-D-thiogalactopyranoside (IPTG).

5. The method according to claim 1, wherein the *E. coli* DSM 27723 are incubated at a temperature of 25° C. to 37° C.

6. The method according to claim 1, wherein the *E. coli* DSM 27723 are cultivated under anaerobic or aerobic conditions.

* * * * *